(12) United States Patent
Tashiro et al.

(10) Patent No.: US 7,434,450 B2
(45) Date of Patent: Oct. 14, 2008

(54) METHOD AND APPARATUS FOR DETECTING EXHAUST GAS SENSOR DEFECT

(75) Inventors: Kenji Tashiro, Toyota (JP); Yasushi Iwazaki, Ebina (JP); Masanobu Kanamaru, Mishima (JP); Hiroshi Sawada, Gotenba (JP); Masaya Kawaji, Susono (JP); Takashi Matsui, Koube (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 66 days.

(21) Appl. No.: 11/448,794

(22) Filed: Jun. 8, 2006

(65) Prior Publication Data

US 2006/0277971 A1    Dec. 14, 2006

(30) Foreign Application Priority Data

Jun. 10, 2005    (JP)    ............................. 2005-171084

(51) Int. Cl.
*G01R 31/30*     (2006.01)
*G01R 31/3163*   (2006.01)
*G01N 27/12*     (2006.01)
*G01N 27/30*     (2006.01)

(52) U.S. Cl. .................. 73/31.05; 702/57; 702/58; 702/116; 73/23.31; 73/23.33; 73/31.06

(58) Field of Classification Search ............. 73/23.31, 73/23.32, 31.05, 31.06; 702/57–59, 100, 702/104, 116
See application file for complete search history.

(56) References Cited

U.S. PATENT DOCUMENTS

| 5,781,878 | A  | * | 7/1998 | Mizoguchi et al. .......... 701/109 |
| 6,711,932 | B2 |   | 3/2004 | Iwazak et al. |
| 6,885,933 | B2 | * | 4/2005 | Lederer et al. .............. 701/109 |
| 2004/0013165 | A1 | * | 1/2004 | Plote et al. .................. 374/172 |
| 2004/0129065 | A1 | * | 7/2004 | Plote et al. .................. 73/117.3 |

FOREIGN PATENT DOCUMENTS

| JP | A-08-021282  | 1/1996  |
| JP | A-08-327586  | 12/1996 |
| JP | A-2003-020989 | 1/2003  |

* cited by examiner

*Primary Examiner*—David A. Rogers
(74) *Attorney, Agent, or Firm*—Kenyon & Kenyon LLP

(57) ABSTRACT

An air-fuel ratio sensor that outputs a sensor signal used for the feedback control of an air-fuel ratio is provided. It is determined whether an element crack is present by applying a reverse voltage to the air-fuel ratio sensor. The value of the sensor signal output from the air-fuel ratio sensor is corrected during a time period "A". The time period "A" consists of a reverse-voltage application time period in which the reverse voltage is applied, and a return time period "T" after application of the reverse voltage ends. The return time period "T" is set based on sensor impedance correlated with the internal resistance of the air-fuel ratio sensor. The return time period "T" decreases as the sensor impedance decreases.

17 Claims, 7 Drawing Sheets

METHOD AND APPARATUS FOR DETECTING EXHAUST GAS SENSOR DEFECT

INCORPORATION BY REFERENCE

The disclosure of Japanese Patent Application No. 2005-171084 filed on Jun. 10, 2005 including the specification, drawings and abstract is incorporated herein by reference in its entirety.

BACKGROUND OF THE INVENTION

1. Field of the Invention

The invention relates to a defect detection apparatus for an exhaust gas sensor. More particularly, the invention relates to a defect detection apparatus and a defect detection method that detect cracks in an element of the exhaust gas sensor.

2. Description of the Related Art

Japanese Patent Application Publication No. JP-A-8-327586 describes an apparatus that detects the defect of an exhaust gas sensor provided in an exhaust passage for an internal combustion engine. More specifically, the apparatus detects the defect of an air-fuel ratio sensor that generates an output corresponding to the oxygen concentration in exhaust gas.

In the aforementioned apparatus, a reverse voltage (i.e., a negative voltage) is applied to the air-fuel ratio sensor at predetermined time intervals so that an electric current flows in the air-fuel ratio sensor in a direction opposite to the normal direction of flow (hereinafter, the electric current flowing in the air-fuel ratio sensor is referred to as "sensor current"). Based on the value of the sensor current when the reverse voltage is applied, it is determined whether a defect, such as a crack in the element, is present in the air-fuel ratio sensor. According to this method, the defect of the air-fuel ratio sensor can be detected easily and accurately.

In the apparatus, the value of the signal output from the air-fuel ratio sensor is not normal during a time period after application of the reverse voltage starts. Therefore, it is not appropriate to use the signal output from the air-fuel ratio sensor in an engine control (for example, the feedback control of the air-fuel ratio) during the time period. That is, if a diagnostic process is performed when the engine control is executed, the engine control may be adversely affected. However, no measures are taken to prevent the engine control from being adversely affected. Thus, the apparatus needs to be improved.

SUMMARY OF THE INVENTION

The invention provides a defect detection apparatus for an exhaust gas sensor, which executes the process of determining whether a defect is present in an exhaust gas sensor, while reducing the adverse influence of the process on an engine control.

A first aspect of the invention relates to an exhaust gas sensor defect detection apparatus. The defect detection apparatus includes an exhaust gas sensor, and a sensor-signal correction device. The exhaust gas sensor outputs a sensor signal used for the control of an internal combustion engine. The sensor-signal correction device corrects the value of the sensor signal output from the exhaust gas sensor. In the defect detection apparatus, a reverse voltage is applied to the exhaust gas sensor to determine whether a defect is present in the exhaust gas sensor. The sensor-signal correction device corrects the value of the sensor signal during a time period after application of the reverse voltage starts.

Generally, when the value of the signal output from the exhaust gas sensor is not normal during the time period after application of the reverse voltage starts, it is not possible to determine whether a defect is present in the exhaust gas sensor. However, in the defect detection apparatus according to the invention, the value of the signal output from the exhaust gas sensor is corrected during the time period. As a result, it can be determined whether a defect is present in the exhaust gas sensor while reducing the adverse influence of the process on the engine control.

A second aspect of the invention relates to a method for detecting a defect in an exhaust gas sensor. The method includes applying a reverse voltage to an exhaust gas sensor, and correcting the value of a sensor signal output from the exhaust gas sensor during a time period after application of the reverse voltage starts.

BRIEF DESCRIPTION OF THE DRAWINGS

The foregoing and further objects, features and advantages of the invention will become apparent from the following description of example embodiments with reference to the accompanying drawings, wherein like numerals are used to represent like elements and wherein.

DETAILED DESCRIPTION OF THE EXEMPLE EMBODIMENTS

Figure 1:
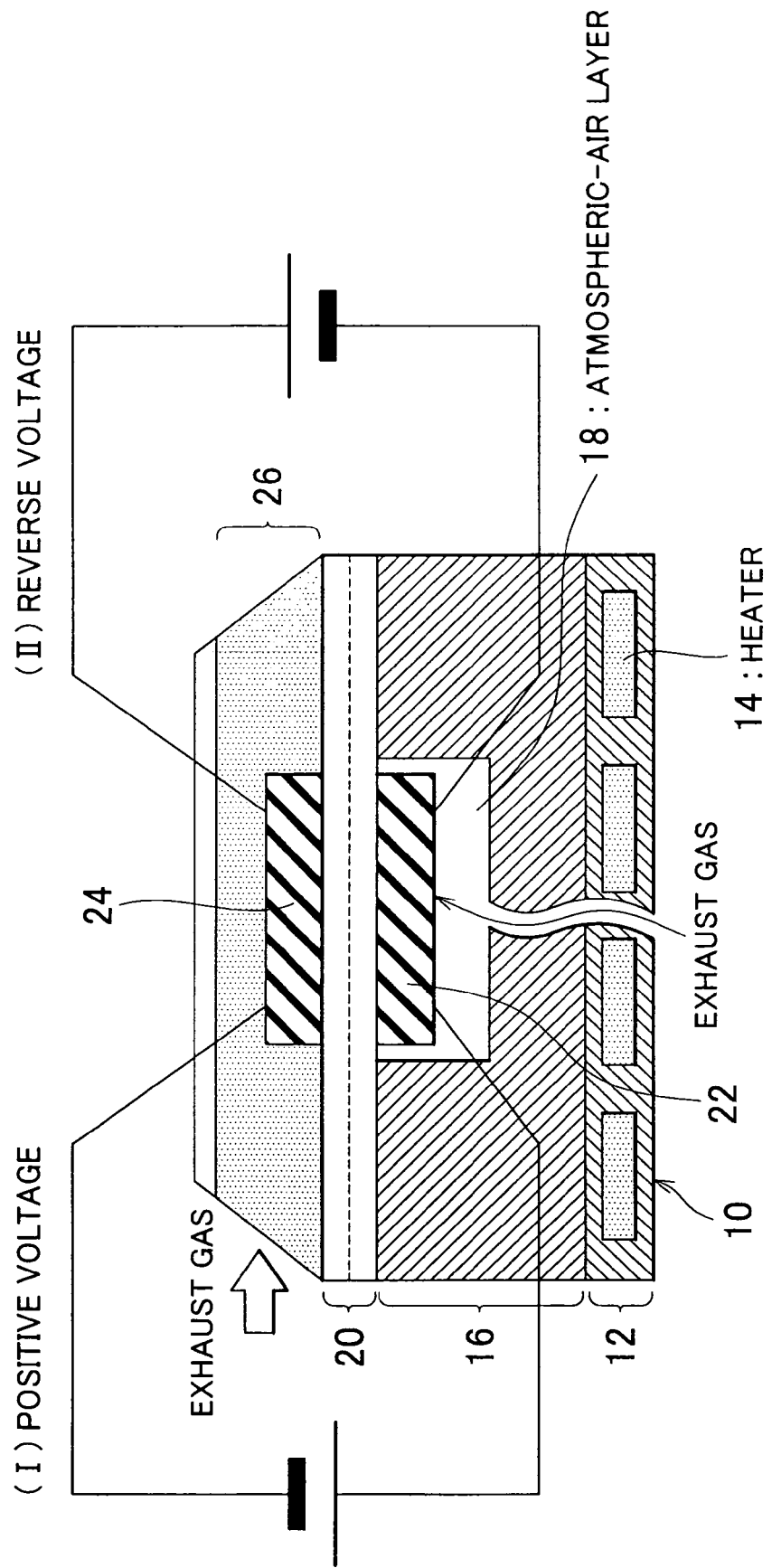
FIG. 1 is a diagram showing the configuration of an air-fuel ratio sensor used in a first embodiment of the invention.

FIG. 1 is a diagram showing the configuration of an air-fuel ratio sensor 10 used in a first embodiment of the invention. More specifically, FIG. 1 is a cross sectional view of a sensor element in the air-fuel ratio sensor 10. The air-fuel ratio sensor 10 includes a sensor element having a cross sectional structure shown in FIG. 1, and a cover (not shown) that protects the sensor element. The air-fuel ratio sensor 10 is fitted to an exhaust passage for an internal combustion engine such that the cover of the sensor element contacts exhaust gas.

A plurality of vent holes is formed in the cover of the air-fuel ratio sensor 10. Exhaust gas flowing in the exhaust passage reaches the sensor element through the vent holes. Therefore, the periphery of the air-fuel ratio sensor 10 (sensor element) contacts the exhaust gas.

The air-fuel ratio sensor 10 includes a heater layer 12. Heaters 14, which heat the sensor element to an active temperature, are embedded in the heater layer 12. In FIG. 1, an atmospheric-air layer formation member 16 is provided on the heater layer 12. The atmospheric-air layer formation member 16 is made of ceramics such as alumina.

An electrolyte layer 20 made of zirconia or the like is provided on the atmospheric-air layer formation member 16. A recess is formed at the center of the upper portion of the atmospheric-air layer formation member 16 so that an atmospheric-air layer 18 is formed. The atmospheric-air layer 18 is separated from a space inside the exhaust passage, by the atmospheric-air layer formation member 16 and the electrolyte layer 20. The atmospheric air flows into the atmospheric-air layer 18 through an atmospheric-air hole (not shown).

An atmospheric-air side electrode 22 is provided on the lower surface of the electrolyte layer 20 such that the atmospheric-air side electrode 22 contacts the atmospheric-air layer 18. An exhaust-gas side electrode 24 is provided on the upper surface of the electrolyte layer 20. The exhaust-gas side electrode 24 is covered with a diffusion resistance layer 26. The diffusion resistance layer 26 is made of porous material. The diffusion resistance layer 26 appropriately regulates the speed at which the exhaust gas flowing in the exhaust passage reaches the exhaust-gas side electrode 24.

As shown in FIG. 1, a positive voltage (I) or a reverse voltage (II) is selectively applied to the air-fuel ratio sensor 10. More specifically, the positive voltage is applied so that the electric potential of the atmospheric-air side electrode 22 is higher than that of the exhaust-gas side electrode 24. In this case, oxygen molecules present on the surface of the exhaust-gas side electrode 24 become oxygen ions, and the oxygen ions move toward the atmospheric-air side electrode 22. As a result, the sensor current corresponding to the oxygen concentration in the exhaust gas, that is, the sensor current corresponding to the air-fuel ratio of the exhaust gas flows between the atmospheric-air side electrode 22 and the exhaust-gas side electrode 24. Therefore, by detecting the value of the sensor current, the air-fuel ratio can be detected.

When the reverse voltage is applied, the electric potential of the exhaust-gas side electrode 24 is higher than that of the atmospheric-air side electrode 22. In this case, oxygen molecules present on the surface of the atmospheric-air side electrode 22 become oxygen ions, and the oxygen ions move toward the exhaust-gas side electrode 24. As a result, a negative current (i.e., reverse current), which is correlated with the oxygen concentration in the atmospheric-air layer 18, flows between the exhaust-gas side electrode 24 and the atmospheric-air side electrode 22. The direction in which the actual electric current flows from the atmospheric-air side electrode 22 to the exhaust-gas side electrode 24 is referred to as "positive direction". The direction in which the actual electric current flows from the exhaust-gas side electrode 24 to the atmospheric-air side electrode 22 is referred to as "negative direction".

Figure 2:
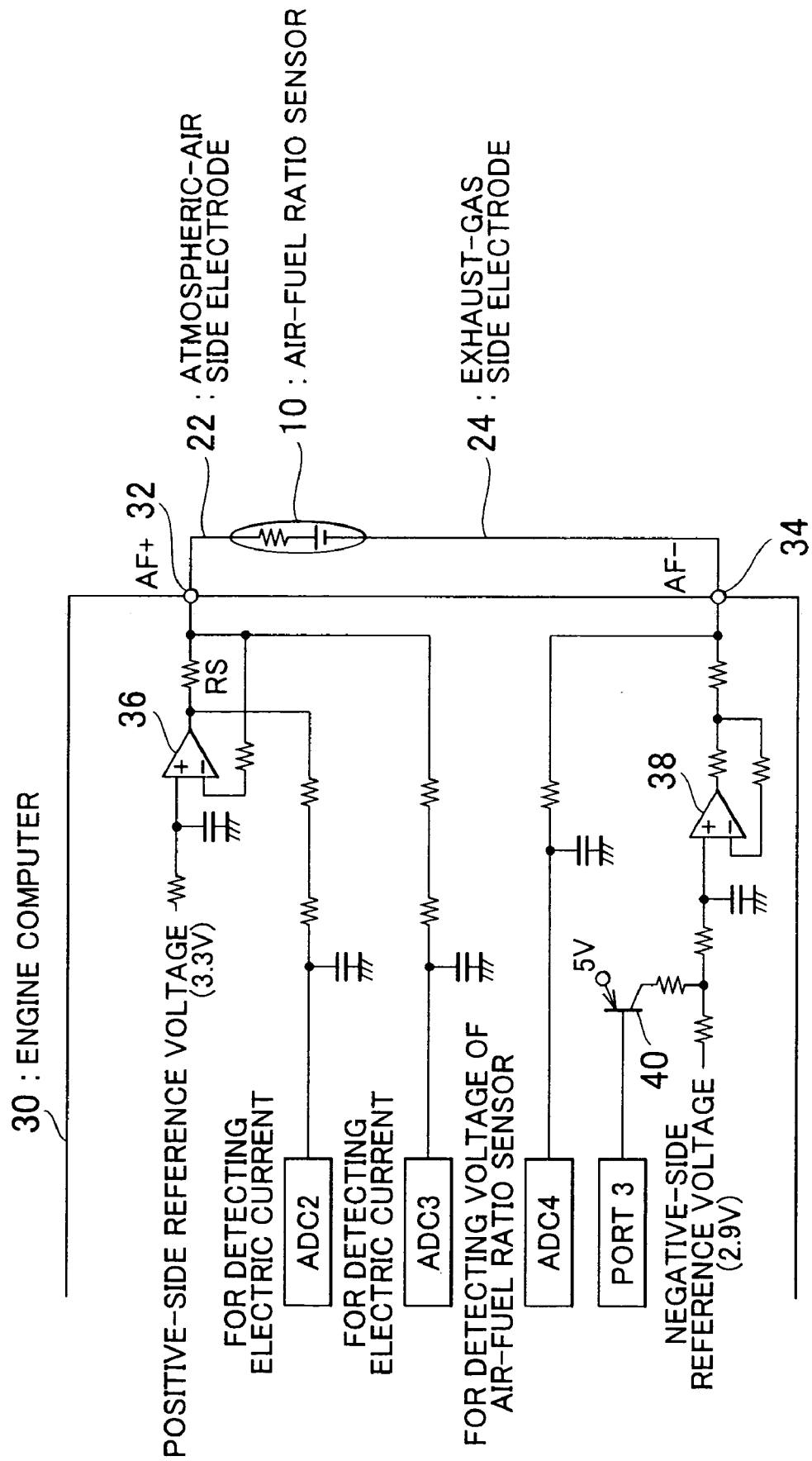
FIG. 2 is a circuit diagram showing the configuration of an engine computer that drives the air-fuel ratio sensor shown in FIG. 1.

FIG. 2 is a circuit diagram showing the configuration of an engine computer 30 that drives the air-fuel ratio sensor 10. In FIG. 2, the circuit includes a positive terminal 32 connected to the atmospheric-air side electrode 22 of the air-fuel ratio sensor 10, and a negative terminal 34 connected to the exhaust-gas side electrode 24 of the air-fuel ratio sensor 10.

The electric potential of the positive terminal 32 is constantly controlled to a positive-side reference voltage (3.3 volts) through feedback, using an operational amplifier 36. The negative terminal 34 is connected to a feedback circuit in which the operational amplifier 36 is used, and a switch circuit in which a transistor 40 is used. The transistor 40 is turned ON and OFF according to the state of a port 3. When the transistor 40 is OFF, the operational amplifier 38 controls the electric potential of the negative terminal 34 to a negative-side reference voltage (2.9 volts). When the transistor 40 is ON, the electric potential input to the operational amplifier 38 increases, and the electric potential of the negative terminal 34 increases to a reverse voltage (approximately 3.7 volts) that is higher than the positive-side reference voltage.

The engine computer 30 has the aforementioned configuration. Thus, by turning the port 3 OFF, the positive voltage of approximately 0.4 volts can be applied to the air-fuel ratio sensor 10. By turning the port 3 ON, the reverse voltage of approximately 0.4 volts can be applied to the air-fuel ratio sensor 10.

The engine computer 30 further includes an ADC2 port, an ADC3 port, and an ADC4 port. The engine computer 30 determines the voltage applied to a shunt resistance RS based on the difference between the electric potential of the ADC2 port and the electric potential of the ADC3 port. By dividing the voltage across the shunt resistance RS by the resistance of the shunt resistance RS, the sensor current can be calculated. Also, by determining the electric potential of the ADC4 port, the electric potential of the negative terminal 34 of the air-fuel ratio sensor 10 can be detected. By abruptly changing the positive voltage applied to the air-fuel ratio sensor 10 by, for example, approximately 0.2 volts, the sensor current is changed in accordance with the change in the voltage. The change in the electric current is determined based on the difference in the electric potential between both ends of the shunt resistance RS. The engine computer 30 calculates impedance of the air-fuel ratio sensor 10 (hereinafter, referred to as "sensor impedance") based on the change in the voltage and the change in the electric current.

The engine computer 30 shown in FIG. 2 detects the sensor current when the positive voltage of approximately 0.4 volts is applied to the air-fuel ratio sensor 10. In this case, based on the sensor current, the air-fuel ratio of the exhaust gas can be detected. The engine computer 30 also detects the sensor current (reverse current) while the reverse voltage of approximately 0.4 volts is applied to the air-fuel ratio sensor 10. In this case, the value of the reverse current is correlated to the oxygen concentration in the atmospheric-air layer 18.

When the air-fuel ratio sensor 10 normally operates, the inside of the atmospheric-air layer 18 remains separated from the space inside the exhaust passage. However, for example, a crack that leads to the atmospheric-air layer 18 (hereinafter, simply referred to as "element crack") may develop in the air-fuel ratio sensor 10. FIG. 1 shows the situation in which an element crack is present in the heater layer 12 and the atmospheric-air formation member 16.

When the internal combustion engine is operating, the pressure inside the exhaust passage is higher than the pressure in the atmospheric-air layer 18 due to the pressure of exhaust gas. Therefore, if an element crack is present in the air-fuel ratio sensor 10, the exhaust gas in the exhaust passage will flow into the atmospheric-air layer 18 through the crack. In this case, the oxygen concentration in the atmospheric-air layer 18 decreases due to the exhaust gas flowing into the atmospheric-air layer 18, as compared to when an element crack is not present.

As described above, the value of the reverse current flowing in the air-fuel ratio 10 corresponds to the oxygen concentration in the atmospheric-air layer 18. Therefore, if a crack is present in the atmospheric-air layer 18, the value of the reverse current decreases as compared to when the air-fuel ratio sensor 10 normally operates. Thus, the engine computer 30 determines whether an element crack is present in the air-fuel ratio sensor 10, by applying the reverse voltage to the air-fuel ratio sensor 10 when the exhaust gas, containing burned gas, flows in the exhaust passage, and determining whether the normal reverse current is generated.

FIGS. 3A and 3B show the change in the sensor current flowing in the air-fuel ratio sensor 10 when the reverse voltage is applied. More specifically, FIG. 3A shows the flag that indicates whether the reverse voltage is applied. FIG. 3B shows the waveforms of the sensor signal output from the air-fuel ratio sensor 10. In FIG. 3B, a solid line indicates the waveform when the internal resistance of the air-fuel ratio sensor 10 is great. A dashed line indicates the waveform when the internal resistance of the air-fuel ratio sensor 10 is small.

When the reverse voltage is applied to the air-fuel ratio sensor 10 to determine whether an element crack is present in the air-fuel ratio sensor 10, the sensor current flows in the reverse direction in the air-fuel ratio sensor 10 as described above. That is, the value of the sensor current flowing in the air-fuel ratio sensor 10 when the reverse voltage is applied is different from that when the positive voltage is applied. The value of the reverse current increases as the internal resistance of the air-fuel ratio sensor 10 decreases. When the reverse voltage is applied, oxygen in the atmospheric-air layer 18 moves from the atmospheric-air side electrode 22 toward the exhaust-gas side electrode 24.

Figure 3:
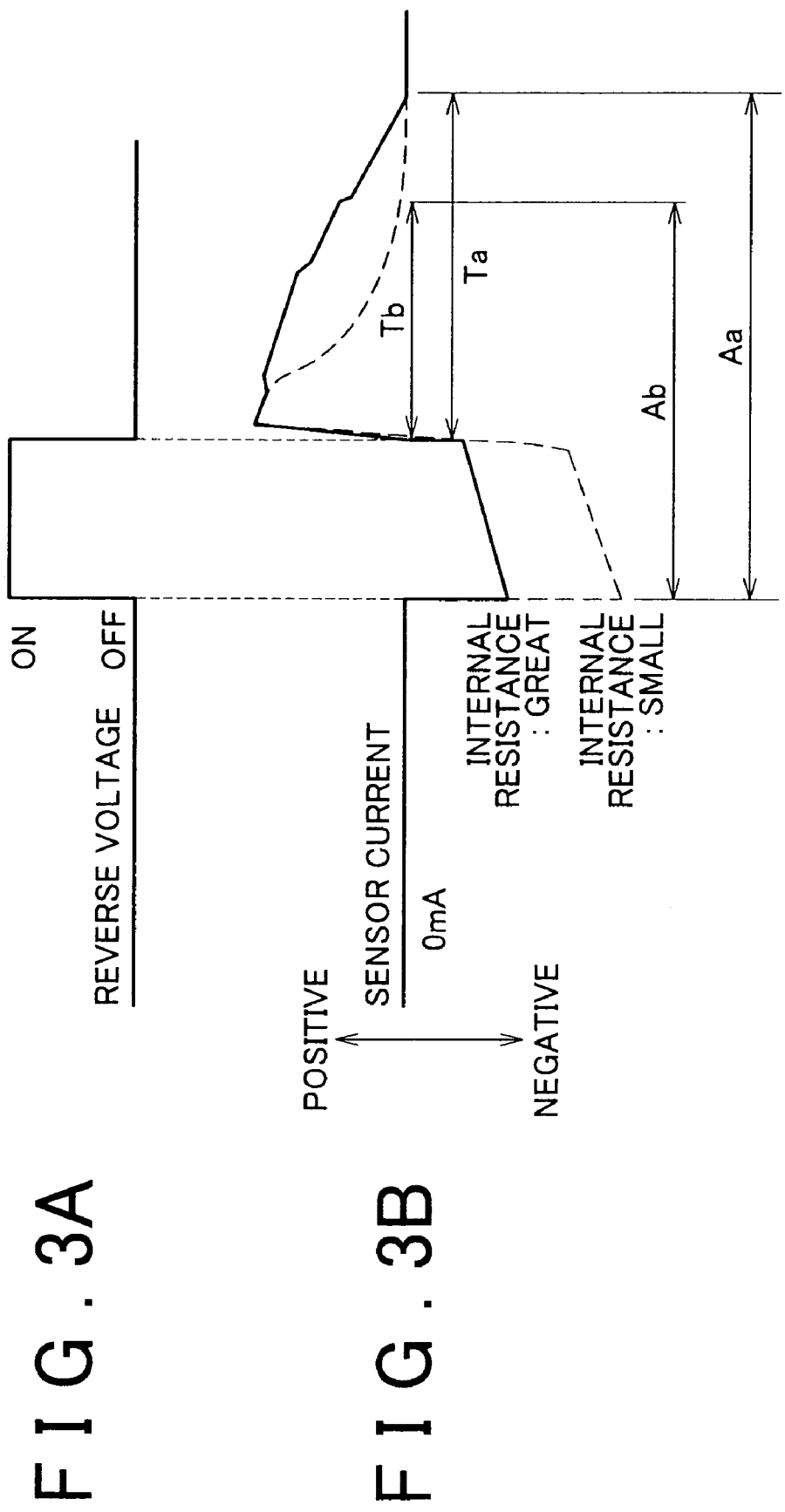
FIGS. 3A and 3B are diagrams explaining a change in a sensor current flowing in the air-fuel ratio sensor when a reverse voltage is applied.

After application of the reverse voltage ends and the positive voltage is applied, surplus oxygen that has remained in the diffusion resistance layer 26 returns to the atmospheric-air layer 18. Therefore, the value of the sensor current does not return to the normal value immediately after application of the reverse voltage ends. Accordingly, during a time period "T" from when application of the reverse voltage ends until when all of the surplus oxygen returns to the atmospheric-air layer 18, the value of the sensor current is different from that when the positive voltage is applied, as shown in FIG. 3. In this specification, the time period "T", from when application of the reverse voltage ends until when the value of the sensor current (sensor signal) returns to a normal value, is referred to as "return time period T".

As described above, during the time period in which the reverse voltage is applied, and during the return time period "T" after application of the reverse voltage ends, the value of the sensor current differs from that when the positive voltage is applied. Therefore, during the aforementioned time periods, it is not appropriate to use the air-fuel ratio of the exhaust gas, which is determined based on the value of the sensor current, in the feedback control of the air-fuel ratio. That is, if the diagnostic test is performed for detecting whether an element crack is present in the air-fuel ratio sensor 10, by applying the reverse voltage to the air-fuel ratio sensor 10, during the feedback control of the air-fuel ratio, the feedback control may be adversely affected.

The return time period "T" changes depending on the internal resistance of the air-fuel ratio sensor 10. More specifically, as the internal resistance of the air-fuel ratio sensor 10 decreases, oxygen ions flow toward the atmospheric-air layer 18 more easily after oxygen molecules that have remained in the diffusion resistance layer 26 become oxygen ions. Therefore, as the internal resistance of the air-fuel ratio sensor 10 decreases, the return time period "T" decreases (refer to Ta, and Tb in FIG. 3). Accordingly, in a defect detection apparatus in this embodiment, during a time period "A" after application of the reverse voltage starts, the value of the signal output from the sensor is corrected, and maintained at the value of the previous sensor signal output immediately before application of the reverse voltage starts. In addition, the return time period "T" is set to decrease as the internal resistance of the air-fuel ratio sensor 10 decreases. The time period "A" consists of a reverse-voltage application time period in which the reverse voltage is applied, and the return time period "T" after application of the reverse voltage ends.

Figure 4:
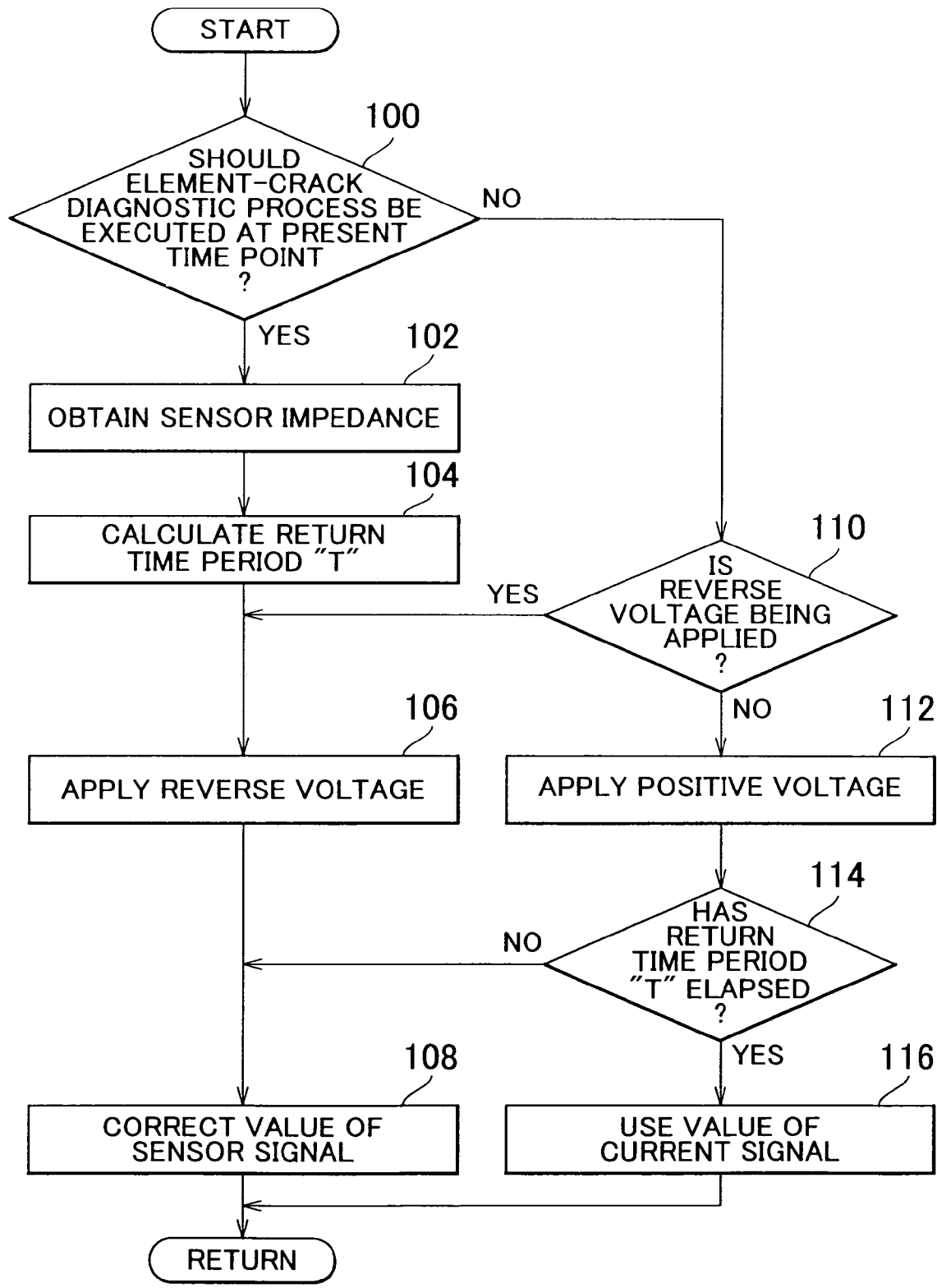
FIG. 4 is a flowchart showing a routine executed in the first embodiment of the invention.

FIG. 4 is the flowchart of a routine executed by the engine computer 30 in the first embodiment to achieve the aforementioned functions. The routine is periodically executed at predetermined time intervals. In the routine shown in FIG. 4, first, it is determined whether an element-crack diagnostic process should be executed at the present time point (step 100). In the element-crack diagnostic process, it is determined whether an element crack is present in the air-fuel ratio sensor 10. In the defect detection apparatus in the embodiment, the element-crack diagnostic process is executed during the feedback control of the air-fuel ratio when the internal combustion engine is in a predetermined operating state in which the air-fuel ratio is stable, for example, when the engine is idling, or when the engine is operating under low load.

If it is determined that the element-crack diagnostic process should be executed at the present time point, the current sensor impedance is obtained (step 102). The engine computer 30 constantly calculates the sensor impedance at predetermined time intervals. In step S102, the newest sensor impedance is obtained.

Figure 5:
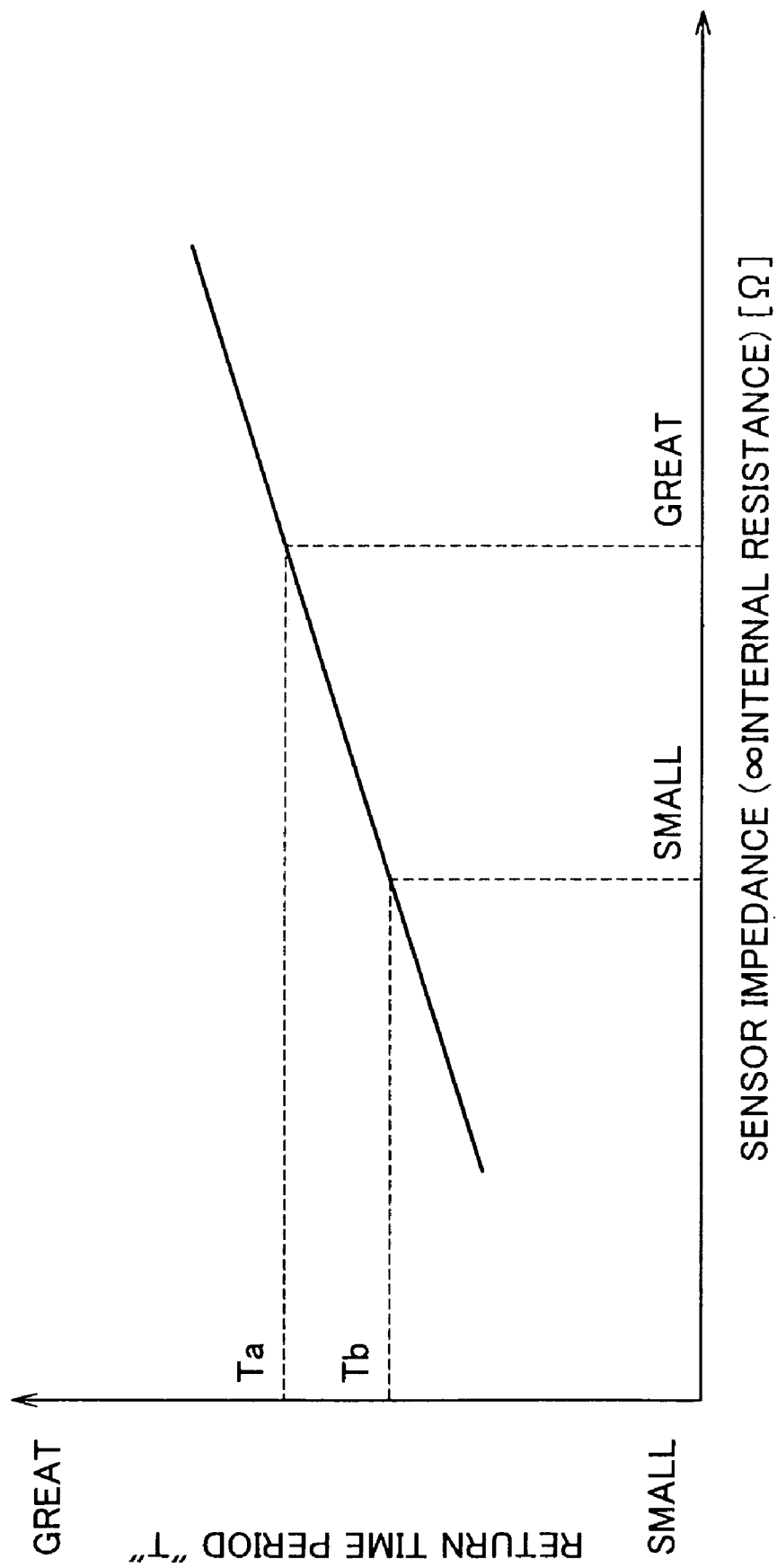
FIG. 5 is an example of a map that is used to calculate a return time period in the routine shown in FIG. 4.

Next, based on the sensor impedance obtained in step 102, the return time period "T" is calculated (step 104). As described above, the signal output from the air-fuel ratio sensor 10 is corrected during the return time period "T" after application of the reverse voltage for the element-crack diagnostic process ends. A map shown in FIG. 5 is stored in the engine computer 30. In the map shown in FIG. 5, the relation between the return time period "T" and the sensor impedance is defined. In the map shown in FIG. 5, the return time period "T" decreases as the sensor impedance decreases. The sensor impedance of the air-fuel ratio sensor 10 is correlated with the internal resistance value of the sensor element. Accordingly, the return time period "T" is set to an appropriate value based on the sensor impedance using the map shown in FIG. 5.

Next, the reverse voltage is applied (step 106). Then, the value of the sensor signal is corrected (step 108). More specifically, the value of the sensor signal that is currently output is replaced with the value of the previous sensor signal that is output immediately before the element-crack diagnostic process starts. This prohibits the value of the current sensor signal from being used for the feedback control of the air-fuel ratio during the period in which the value of the current sensor signal is corrected.

If it is determined that the element-crack diagnostic process should not be executed at the present time point in step 100, it is determined whether the reverse voltage is being applied (step 110). If it is determined that the reverse voltage is being applied, the application of the reverse voltage and the correction of the value of the sensor signal continue (step 106 and step 108). If it is determined that the application of the reverse voltage has ended, the positive voltage is applied as usual (step 112).

If it is determined that the application of the reverse voltage has ended, it is determined whether the return time period "T" has elapsed (step 114). If it is determined that the return time period T has not elapsed, the correction of the value of the sensor signal continues (step 108). If it is determined that the return time period "T" has elapsed, the value of the current sensor signal is used for the feedback control of the air-fuel ratio (step 116).

As described above, according to the routine shown in FIG. 4, during the time period in which the reverse voltage is applied, and during the return time period "T" after application of the reverse voltage ends, the value of the current sensor signal is not used for the feedback control of the air-fuel ratio, and the value of the current sensor signal is replaced with the value of the last sensor signal output immediately before application of the reverse voltage starts. That is, when the element-crack diagnostic process is executed during the feedback control of the air-fuel ratio, the value of the sensor signal output from the sensor is corrected during the period in which the value of the sensor signal is not normal. This reduces the adverse influence that the element-crack diagnostic process has on the feedback control of the air-fuel ratio.

Also, according to the aforementioned routine, the return time period "T" is changed based on the sensor impedance correlated with the internal resistance of the air-fuel ratio sensor 10. Therefore, when the element-crack diagnostic process is executed, the time period in which the value of the sensor signal needs to be corrected can be appropriately determined. As a result, the element-crack diagnostic process can be executed during the feedback control while reliably reducing the adverse influence on the feedback control.

In the aforementioned first embodiment, when the engine computer 30 executes the routine shown in FIG. 4, "the sensor-signal correction means" is realized.

Next, a second embodiment of the invention will be described with reference to FIG. 6. In the defect detection apparatus in the second embodiment, the hardware configuration shown in FIGS. 1 and 2 is employed, and the engine computer 30 executes a routine shown in FIG. 6, instead of the routine shown in FIG. 4.

When the internal combustion engine is operating, a purge control is executed. In the purge control, fuel vapor adsorbed by a canister is purged to an intake passage, by appropriately executing the duty control of a purge VSV. When the purge control is executed, the air-fuel ratio is low. Using the signal output from the air-fuel ratio sensor, the engine computer 30 determines the amount by which the air-fuel ratio changes (i.e., change amount) when purge air is introduced by opening the purge VSV. The engine computer 30 determines and learns the ratio between the change amount and a purge rate, as a purge learning value (hereinafter, this process will be referred to as "purge learning process").

The purge control is generally executed when the air fuel ratio is stable, for example, when the internal combustion engine is operating under low load. As described above, the value of the sensor signal is not normal during the period in which the reverse voltage is applied to execute the element-crack diagnostic process, and during the return time period "T" after application of the reverse voltage ends (i.e., during the time period "A"). Therefore, to reduce the adverse influence on the feedback control, the element-crack diagnostic process is executed when the air-fuel ratio is stable. As a result, the time period in which the purge control is executed may overlap the time period in which the element-crack diagnostic process is executed.

If the purge learning process is executed during the time period "A", the purge learning process cannot be accurately executed, because the value of the sensor signal is not normal. Also, as in the first embodiment, the value of the current sensor signal may be maintained at the value of the previous sensor signal output immediately before application of the reverse voltage starts, during the time period "A". That is, the value of the current sensor signal is not used during the time period "A". In this case, because the value of the sensor signal is not affected by the purge control, the purge learning value deviates from the actual value. If the purge control is executed using the deviated value, the level of exhaust gas may deteriorate, and the engine may, for example, stall. Accordingly, in the second embodiment, execution of the purge learning process is prohibited during the time period "A".

Figure 6:
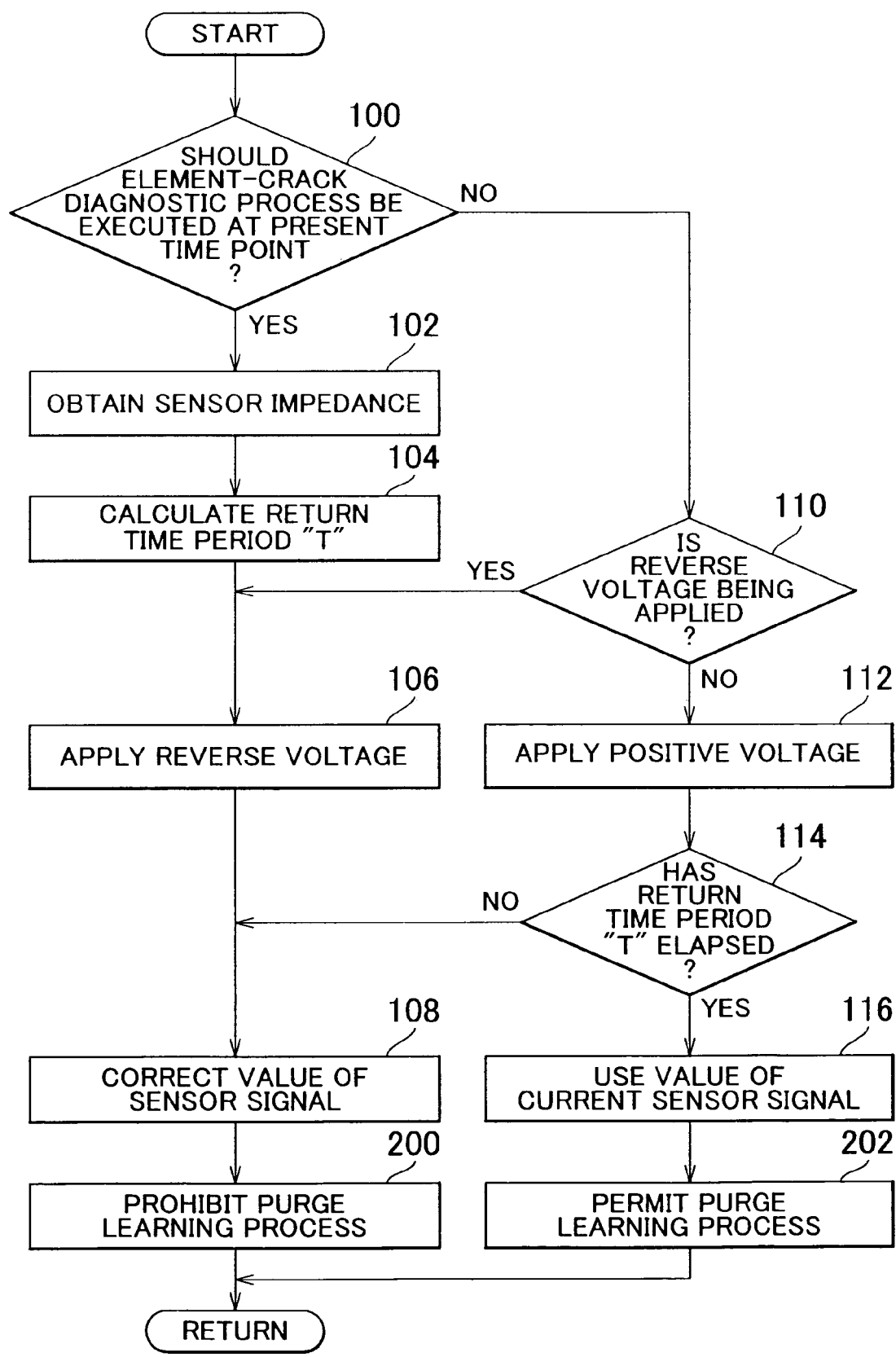
FIG. 6 is a flowchart showing a routine executed in a second embodiment of the invention.

FIG. 6 is the flowchart of a routine executed by the engine computer 30 in the second embodiment to perform the aforementioned functions. This routine is periodically executed at predetermined time intervals. In the flowchart in FIG. 6, the same steps as those in FIG. 4 are denoted by the same reference numerals, and description thereof will be omitted or simplified.

In the routine shown in FIG. 6, if it is determined that the element-crack diagnostic process should be executed for the air-fuel ratio sensor 10 at the present time point (step 100), the steps 102 to 108 are executed. In addition, the execution of the purge learning process is prohibited (step 200). That is, if an affirmative determination is made in step 100, the update of the purge learning value is prohibited even if the purge control is executed. Alternatively, it is also possible to prohibit the purge control in step 200 instead of the execution of the purge learning process.

Even in the case where the routine starts after the time point at which the element-crack diagnostic process should be executed, step 200 is executed if it is determined that the reverse voltage is being applied in step 110, or if it is determined that the return time period "T" has not elapsed in step 114. If it is determined that the return time period "T" has elapsed in step 114, the execution of the purge learning process is permitted (step 202).

As described above, according to the routine shown in FIG. 6, it is possible to prevent the purge learning value from deviating from the actual value when the reverse voltage is applied during the element-crack diagnostic process. This reduces the possibility that the level of exhaust gas deteriorates, and an engine stall or the like occurs due to the deviation of the purge learning value from the actual value.

In the second embodiment, when the engine computer 30 executes the routine shown in FIG. 6, "the learning prohibition means" is realized.

In the first embodiment and the second embodiment, during the time period "A" after application of the reverse voltage starts, the value of the current sensor signal is maintained at the value of the last sensor signal output immediately before application of the reverse voltage starts. However, the method of correcting the value of the sensor signal during the time period "A" is not limited to the aforementioned method. That is, for example, during the time period "A", an air-fuel ratio control (open-loop control) may be executed using a basic air-fuel ratio that is calculated based on the amount of intake air and the amount of injected fuel, and without using the value of the current sensor signal and the value of the previous sensor signal output from the air-fuel ratio sensor 10. Alternatively, during the time period "A", the feedback control of the air-fuel ratio may be executed using an estimated air-fuel ratio that will be described below with reference to FIG. 7.

Figure 7:
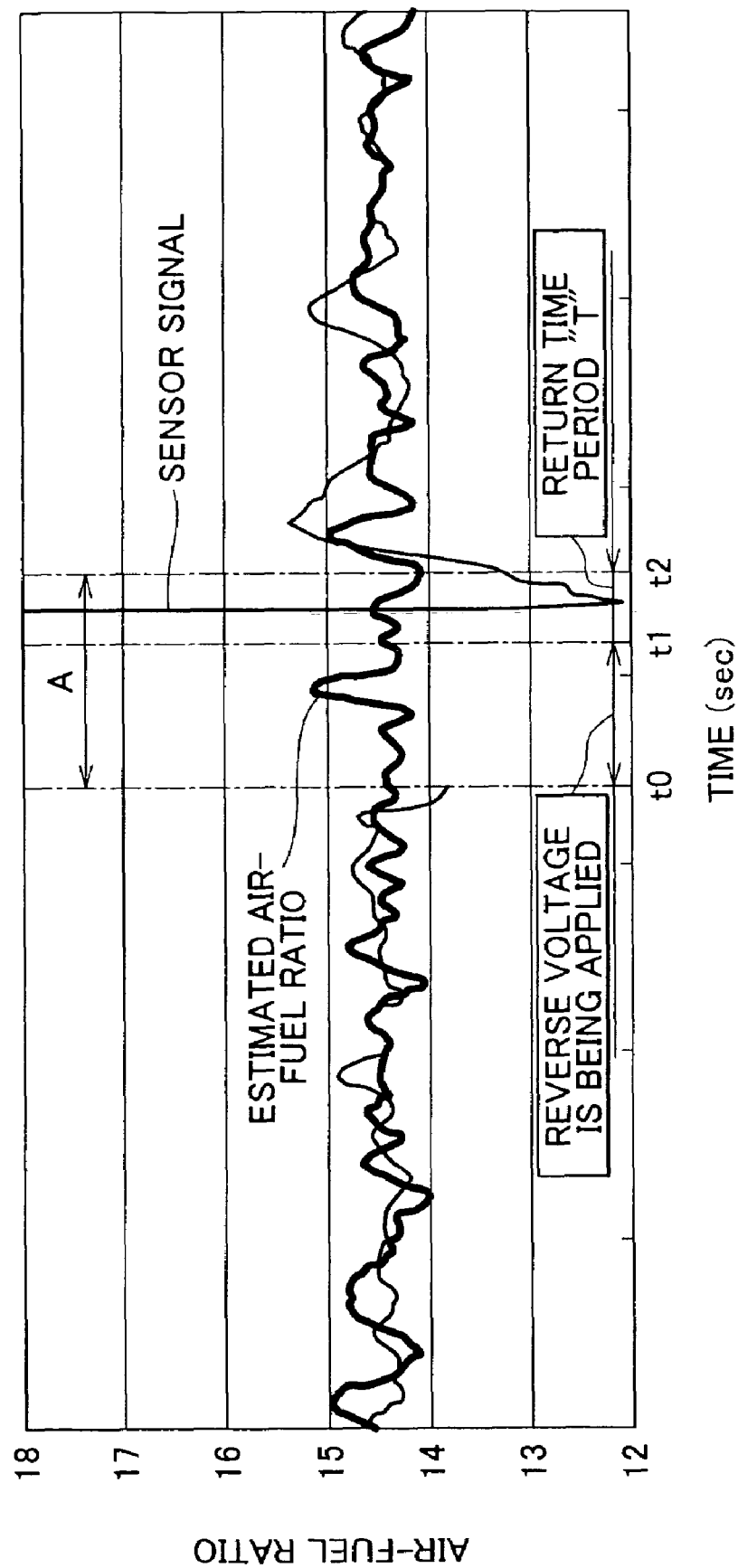
FIG. 7 is a timing chart showing the situation in which a feedback control is executed using an estimated air-fuel ratio during a time period after application of the reverse voltage starts in a modified example of the invention.

As shown in FIG. 7, the value of the sensor signal output from the air-fuel ratio sensor 10 is not normal during the time period in which the reverse voltage is applied (i.e., the time period from time point t0 until time point t1) and during the return time period "T" (i.e., the time period from time point t1 until time point t2) after application of the reverse voltage ends. The waveform of the sensor signal is indicated by a thin solid line in FIG. 7. Thus, during the time period "A", the feedback control may be executed using the estimated air-fuel ratio, instead of using the values of the current sensor signal and the previous sensor signal. The waveform of the estimated air-fuel ratio is indicated by a thick line in FIG. 7. The estimated air-fuel ratio is obtained by correcting the basic air-fuel ratio using an air-fuel ratio learning value. The basic air-fuel ratio is calculated based on the amount of intake air and the amount of injected fuel. The air-fuel ratio learning value is obtained taking into account, for example, the amount of fuel adhering to a wall surface. When this method is used, the adverse influence that the element-crack diagnostic process has on the feedback control is reduced during the time period "A", as compared to when the value of the sensor signal, which is maintained at a constant value, is used for the feedback control of the air-fuel ratio. As a result, the reverse voltage can be applied without causing any problem during the feedback control, regardless of the operating state of the internal combustion engine. Also, the reverse voltage can be applied for a long time period.

In the first embodiment and the second embodiment, it is determined whether an element crack is present in the air-fuel ratio sensor. However, it may be determined whether an element crack is present in other components. For example, it may be determined whether an element crack is present in an oxygen sensor (i.e., a sensor that generates an output based on whether the air-fuel ratio of exhaust gas is high or low).

What is claimed is:

1. An exhaust gas sensor defect detection apparatus, comprising:
an exhaust gas sensor that outputs a sensor signal used for a control of an internal combustion engine; and a sensor-signal correction device that corrects a value of the sensor signal output from the exhaust gas sensor, wherein:

a reverse voltage is applied to the exhaust gas sensor to determine whether a defect is present in the exhaust gas sensor;

the sensor-signal correction device corrects the value of the sensor signal output from the exhaust gas sensor during a time period after application of the reverse voltage starts;

the time period consists of a reverse-voltage application time period in which the reverse voltage is applied, and a return time period from when application of the reverse voltage ends until when the value of the sensor signal returns to a normal value; and the return time period is set to decrease as an the internal resistance of the exhaust gas sensor decreases.

2. The exhaust gas sensor defect detection apparatus according to claim 1, wherein the control of the internal combustion engine is a feedback control of an air-fuel ratio of the internal combustion engine.

3. The exhaust gas sensor defect detection apparatus according to claim 1, further comprising:

a learning prohibition device that prohibits execution of a purge learning process during the time period.

4. The exhaust gas sensor defect detection apparatus according to claim 1, wherein the reverse voltage is applied when the air-fuel ratio of the internal combustion engine is stable.

5. The exhaust gas sensor defect detection apparatus according to claim 1, wherein the reverse voltage is applied when the internal combustion engine is idling.

6. The exhaust gas sensor defect detection apparatus according to claim 1, wherein the internal resistance of the exhaust gas sensor is determined based on a change in a voltage applied to the exhaust gas sensor during a predetermined time period, and a change in an electric current flowing in the exhaust gas sensor, resulting from the change in the voltage.

7. The exhaust gas sensor defect detection apparatus according to claim 1, wherein the value of the sensor signal output from the exhaust gas sensor during the time period is corrected to a value of the sensor signal that is output immediately before application of the reverse voltage starts.

8. The exhaust gas sensor defect detection apparatus according to claim 1, wherein the value of the sensor signal output from the exhaust gas sensor during the time period is corrected based on an amount of air taken into the internal combustion engine and an amount of injected fuel.

9. The exhaust gas sensor defect detection apparatus according to claim 1, wherein the exhaust gas sensor includes:

an exhaust-gas side electrode that contacts exhaust gas in an exhaust passage of the internal combustion engine, an atmospheric-air layer formation member that forms an atmospheric-air layer in the exhaust passage, an atmospheric-air side electrode that contacts the atmospheric-air layer, and an electrolyte layer, provided between the exhaust-gas side electrode and the atmospheric-air side electrode, which allows oxygen ions to move between the exhaust-gas side electrode and the atmospheric-air side electrode; and wherein the reverse voltage is applied between the exhaust-gas side electrode and the atmospheric-air side electrode so that an electric potential of the exhaust-gas side electrode is higher than that of the atmospheric-air side electrode.

10. The exhaust gas sensor defect detection apparatus according to claim 9, wherein the atmospheric-air layer is separated from a space inside the exhaust passage of the internal combustion engine, by the atmospheric-air layer formation member and the electrolyte layer, and atmospheric air flows into the atmospheric-air layer.

11. The exhaust gas sensor defect detection apparatus according to claim 9, further comprising:

a diffusion resistance layer made of porous material, which covers the exhaust-gas side electrode.

12. The exhaust gas sensor defect detection apparatus according to claim 9, further comprising:

a heater layer, provided on the atmospheric-air layer formation member, which heats the exhaust gas sensor.

13. A method for detecting a defect in an exhaust gas sensor, comprising:

applying a reverse voltage to an exhaust gas sensor that outputs a sensor signal used for a control of an internal combustion engine to determine whether a defect is present in the exhaust gas sensor; and correcting a value of the sensor signal output from the exhaust gas sensor during a time period after application of the reverse voltage starts wherein:

the time period consists of a reverse-voltage application time period in which the reverse voltage is applied, and a return time period from when application of the reverse voltage ends until when the value of the sensor signal returns to a normal value; and the return time period is set to decrease as an the internal resistance of the exhaust gas sensor decreases.

14. The method for detecting a defect in an exhaust gas sensor according to claim 13, further comprising:

determining an internal resistance of the exhaust gas sensor; and calculating the time period based on the internal resistance of the exhaust gas sensor, wherein the internal resistance of the exhaust gas sensor is determined based on a change in a voltage applied to the exhaust gas sensor during a predetermined time period, and a change in an electric current flowing in the exhaust gas sensor, resulting from the change in the voltage.

15. The method for detecting a defect in an exhaust gas sensor according to claim 13, further comprising:

prohibiting execution of a purge learning process during the time period.

16. The method for detecting a defect in an exhaust gas sensor according to claim 13, wherein the value of the sensor signal output from the exhaust gas sensor during the time period is corrected to a value of the sensor signal output from the exhaust gas sensor immediately before application of the reverse voltage starts, or the value of the sensor signal output from the exhaust gas sensor during the time period is corrected based on an amount of air taken into the internal combustion engine and an amount of injected fuel.

17. An exhaust gas sensor defect detection apparatus, comprising:

an exhaust gas sensor that outputs a sensor signal used for a control of an internal combustion engine; and a sensor-signal correction means for correcting a value of the sensor signal output from the exhaust gas sensor, wherein a reverse voltage is applied to the exhaust gas sensor to determine whether a defect is present in the exhaust gas sensor;

the sensor-signal correction means corrects the value of the sensor signal output from the exhaust gas sensor during a time period after application of the reverse voltage starts;

the time period consists of a reverse-voltage application time period in which the reverse voltage is applied, and a return time period from when application of the reverse voltage ends until when the value of the sensor signal output by the exhaust gas sensor returns to a normal value; and the return time period is set to decrease as the internal resistance of the exhaust gas sensor decreases.

* * * * *

UNITED STATES PATENT AND TRADEMARK OFFICE
CERTIFICATE OF CORRECTION

PATENT NO. : 7,434,450 B2  Page 1 of 1
APPLICATION NO. : 11/448794
DATED : October 14, 2008
INVENTOR(S) : Kenji Tashiro et al.

It is certified that error appears in the above-identified patent and that said Letters Patent is hereby corrected as shown below:

| Claim | Column | Line | |
|-------|--------|------|---|
| 1 | 9 | 16 | After "as" delete "an". |
| 13 | 10 | 30 | After "as" delete "an". |

Signed and Sealed this

Second Day of June, 2009

JOHN DOLL
*Acting Director of the United States Patent and Trademark Office*